United States Patent
Nilsson (10) Patent No.: US 10,398,539 B2
(45) Date of Patent: Sep. 3, 2019

(54) SYSTEM AND METHOD FOR ALIGNING VIRTUAL DENTAL MODELS

(75) Inventor: Urban Nilsson, Halta (SE)

(73) Assignee: Nobel Biocare Services AG, Kloten (CH)

( * ) Notice: Subject to any disclaimer, the term of this patent is extended or adjusted under 35 U.S.C. 154(b) by 167 days.

(21) Appl. No.: 13/257,944

(22) PCT Filed: Mar. 19, 2010

(86) PCT No.: PCT/EP2010/001728
§ 371 (c)(1),
(2), (4) Date: Oct. 27, 2011

(87) PCT Pub. No.: WO2010/105837
PCT Pub. Date: Sep. 23, 2010

(65) Prior Publication Data
US 2012/0040311 A1    Feb. 16, 2012

(30) Foreign Application Priority Data
Mar. 20, 2009  (EP) .................................. 09004003

(51) Int. Cl.
*A61C 9/00* (2006.01)
*A61C 19/05* (2006.01)
(Continued)

(52) U.S. Cl.
CPC .......... *A61C 19/05* (2013.01); *A61C 13/0004* (2013.01); *G16H 20/40* (2018.01); *A61C 9/0006* (2013.01)

(58) Field of Classification Search
CPC ......... A61C 9/00; A61C 9/004; A61C 9/0006; A61C 9/0046; G06T 2219/2004; G06T 7/0024
(Continued)

(56) References Cited

U.S. PATENT DOCUMENTS 2,171,695 A * 9/1939 Harper ............................ 433/42
6,152,731 A * 11/2000 Jordan et al. ................... 433/69
(Continued)

FOREIGN PATENT DOCUMENTS

| WO | WO 2006/031096 | 3/2006 |
|---|---|---|
| WO | WO 2008/083857 | 7/2008 |
| WO | WO 2010/105837 | 9/2010 |

OTHER PUBLICATIONS

International Search Report for International Application No. PCT/EP2010/001728 dated Aug. 31, 2010.
(Continued)

*Primary Examiner* — Wade Miles
*Assistant Examiner* — Matthew P Saunders
(74) *Attorney, Agent, or Firm* — Knobbe Martens Olson & Bear LLP (57) ABSTRACT

A method of aligning a virtual model of an upper jaw (502) and a virtual model of a lower jaw (504) in a bite position includes matching first facial surfaces (520b) of a virtual model of a side impression (506) with facial surfaces (520a) of the virtual model of the upper jaw (502) and matching second facial surfaces (521b) of a virtual model of a side impression (506) with facial surfaces (521a) of the virtual model of the lower jaw (504). At least a portion of the first facial surfaces (520b) of the virtual model of the side impression (506) are the same as the facial surfaces (520a) of the virtual model of the upper jaw (502). At least a portion of the second facial surfaces (521b) of the virtual model of the side impression (506) are the same as the facial surfaces (521a) of the virtual model of the lower jaw (504).

17 Claims, 6 Drawing Sheets

(51) Int. Cl.
*G16H 20/40* (2018.01)
*A61C 13/00* (2006.01)

(58) Field of Classification Search
USPC .................................................. 433/213–223
See application file for complete search history.

(56) References Cited

U.S. PATENT DOCUMENTS

| | | | | |
|---|---|---|---|---|
| 6,206,693 | B1* | 3/2001 | Hultgren | A61C 9/0006 |
| | | | | 433/38 |
| 6,219,403 | B1* | 4/2001 | Nishihara | A61N 5/1048 |
| | | | | 378/205 |
| 6,582,229 | B1 | 6/2003 | Miller et al. | 433/213 |
| 6,671,539 | B2 | 12/2003 | Gateno et al. | |
| 6,957,118 | B2* | 10/2005 | Kopelman et al. | 700/118 |
| 6,979,196 | B2* | 12/2005 | Nikolskiy | A61C 19/05 |
| | | | | 433/214 |
| 7,058,213 | B2* | 6/2006 | Rubbert | A61C 7/00 |
| | | | | 348/207.99 |
| 7,156,661 | B2* | 1/2007 | Choi et al. | 433/213 |
| 7,220,124 | B2 | 5/2007 | Taub et al. | |
| 7,228,191 | B2* | 6/2007 | Hofmeister et al. | 700/98 |
| 7,362,890 | B2* | 4/2008 | Scharlack et al. | 382/128 |
| 7,762,814 | B2 | 7/2010 | Van der Zel | |
| 7,925,374 | B2 | 4/2011 | Andersson et al. | |
| 8,234,000 | B2* | 7/2012 | Andersson et al. | 700/98 |
| 8,255,071 | B2 | 8/2012 | Kaigler | |
| 8,425,229 | B2 | 4/2013 | Nilsson et al. | |
| 2002/0064759 | A1* | 5/2002 | Durbin | A61C 9/00 |
| | | | | 433/213 |
| 2002/0081554 | A1* | 6/2002 | Marshall et al. | 433/213 |
| 2002/0094509 | A1* | 7/2002 | Durbin | A61C 9/00 |
| | | | | 433/213 |
| 2004/0015327 | A1 | 1/2004 | Sachdeva et al. | |
| 2004/0133293 | A1* | 7/2004 | Durbin | A61C 13/0013 |
| | | | | 700/98 |
| 2004/0146830 | A1 | 7/2004 | Weinstein | |
| 2004/0220691 | A1* | 11/2004 | Hofmeister | A61C 13/0004 |
| | | | | 700/98 |
| 2005/0021163 | A1* | 1/2005 | Gu | G06T 7/33 |
| | | | | 700/95 |
| 2005/0048432 | A1* | 3/2005 | Choi | A61C 7/00 |
| | | | | 433/24 |
| 2005/0117693 | A1 | 6/2005 | Miyano | |
| 2005/0153257 | A1* | 7/2005 | Durbin | A61C 19/05 |
| | | | | 433/68 |
| 2005/0186540 | A1* | 8/2005 | Taub et al. | 433/223 |
| 2005/0250075 | A1 | 11/2005 | Taub et al. | |
| 2005/0251281 | A1* | 11/2005 | O'Brien et al. | 700/119 |
| 2006/0004477 | A1* | 1/2006 | Kopelman et al. | 700/118 |
| 2006/0122719 | A1* | 6/2006 | Kopelman et al. | 700/98 |
| 2006/0212260 | A1* | 9/2006 | Kopelman et al. | 702/152 |
| 2006/0263738 | A1* | 11/2006 | Kuo | 433/24 |
| 2007/0207441 | A1* | 9/2007 | Lauren | 433/213 |
| 2008/0026338 | A1 | 1/2008 | Cinader | |
| 2008/0206705 | A1* | 8/2008 | Kaza | A61C 7/002 |
| | | | | 433/71 |
| 2009/0220916 | A1* | 9/2009 | Fisker et al. | 433/201.1 |
| 2010/0105011 | A1* | 4/2010 | Karkar | A61C 1/084 |
| | | | | 433/215 |
| 2010/0151417 | A1 | 6/2010 | Nilsson et al. | |
| 2011/0196524 | A1 | 8/2011 | Giasson et al. | |
| 2012/0183183 | A1 | 7/2012 | Jouhikainen | |
| 2013/0230818 | A1 | 9/2013 | Matov et al. | |

OTHER PUBLICATIONS

International Preliminary Report on Patentability and Written Opinion of the International Searching Authority for International Application No. PCT/EP2010/001728 dated Sep. 29, 2011.
Extended European Search Report for European Patent Application No. 09004003.1 dated Aug. 27, 2009.

* cited by examiner

SYSTEM AND METHOD FOR ALIGNING VIRTUAL DENTAL MODELS

BACKGROUND

Field

The present application is generally related to dental modeling, and more particularly to a system and method for matching virtual models of teeth in occlusive position.

Description of Related Technology

Physical and virtual dental models can be used, inter alia, to design orthodontic appliances, to plan or adjust movement of teeth with orthodontic appliances, and to finalize dental prostheses. Orthodontists, dentists, and dental technicians prefer that models of the upper and lower jaws can be viewed in the bite position.

Aligning virtual models of upper and lower jaws in an occlusive relationship currently uses three impressions: (1) a bite impression including occlusal surfaces of the upper jaw on one side and occlusal surfaces of the lower jaw on an opposite side; (2) an impression of the upper jaw including occlusal surfaces of the upper jaw; and (3) an impression of the lower jaw including occlusal surfaces of the lower jaw. Stone models or plaster casts produced from the impressions of the upper and lower jaws may be simultaneously scanned or imaged with the bite impression placed therebetween or as aligned by the bite impression in order to produce virtual models of the bite position, for example as described in U.S. Pat. Nos. 6,979,196 and 7,362,890, each incorporated herein by reference in its entirety. The stone models may also be scanned or imaged individually to produce individual virtual models of the upper and lower jaws. One procedure for aligning virtual models of upper and lower jaws in an occlusive relationship involves scanning or imaging four surfaces (each side of the bite impression, the impression of the upper jaw, and the impression of the lower jaw), and then matching the features of their occlusal surfaces. However, the large number of cusps, ridges, etc. can unduly complicate such matching procedures. Additionally, scanning the surfaces of these four impressions can be time consuming and/or costly. Another procedure involves moving the virtual models around until the amount of overlap of the upper and lower jaws is minimized. However, such procedures do not necessarily produce an accurate occlusive relationship.

SUMMARY

In certain embodiments, the devices and methods described herein can advantageously reduce the number of scans, for example from four to three. In certain such embodiments, scanning comprises scanning an impression of a upper jaw, an impression of a lower jaw, and a side (e.g., facial side) impression rather than scanning the impression of the upper jaw, the impression of the lower jaw, a first side of the bite impression (e.g., maxillary occlusal side), and a second side of the bite impression (e.g., mandibular occlusal side). In certain such embodiments, the scan error may also be reduced by reducing the number of scans, for example because errors may be induced with additional scanning. In certain embodiments, using a wide scan area (e.g., the entire facial surfaces of maxillary and mandibular teeth, even including soft tissue features such as gingival ridges) can improve accuracy. For example, matching errors at the location of the side bite can be magnified at the opposite side of the mouth. In such embodiments, the side impression can include impressions of surfaces at locations where accuracy is of greatest importance, such as at an area for a dental restoration.

A bite impression generally includes some thickness between occlusal surfaces of the teeth (e.g., enabling scanning of the occlusal surfaces), but such thickness can cause errors during matching because the bite impression will indicate that the upper and lower jaws should be separated by that thickness in the bite position, which is not the true occlusive position. Thus, the practitioner cannot be sure that the registered bite position is the true occlusive position in which opposing occlusal surfaces of opposing teeth contact each other. In certain applications such as designing prosthesis, the true occlusive position can be important (e.g., to ensure that the prosthesis provides a functional bite, to indicate the space available for designing prostheses, etc.). Moreover, bite impressions are generally soft (e.g., due to the impression material and/or because they are thin) and can deform. In certain embodiments, the devices and methods described herein can advantageously reduce error caused by impression material, at least because there is little or no impression material between occlusal surfaces and/or because excess impression material beyond the facial surfaces can provide additional matching information.

In certain embodiments, a method comprises scanning an side impression to form a digital side impression model. The digital side impression model is substantially free of occlusal surfaces and of occlusive surfaces (i.e., opposing occlusal surfaces that contact each other). The digital side impression model comprises facial surfaces of at least a portion of a maxillary tooth and facial surfaces of at least a portion of a mandibular tooth. The method further comprises scanning an impression of at least a portion of an upper dental arch to create a digital upper arch model. The digital upper arch model comprises facial surfaces of at least a portion of the maxillary tooth. The method further comprises matching at least part of the facial surfaces of the maxillary tooth of the digital side impression model and at last a part of the same facial surfaces of the maxillary tooth of the digital upper arch model. Hence, the same surfaces of the maxillary tooth and/or other features, such as soft tissue, of the upper jaw are captured in the side impression and the impression of the upper arch. The method further comprises scanning an impression of at least a portion of a lower dental arch to create a digital lower arch model. The digital lower arch model comprises facial surfaces of at least a portion of the mandibular tooth. The method further comprises matching at least part of the facial surfaces of the mandibular tooth of the digital side impression model and at least a part of the same facial surfaces of the mandibular tooth of the digital lower arch model. Hence, at least portions of the same surfaces of the mandibular tooth and/or other features, such as soft tissue, of the lower jaw are captured in the side impression and the impression of the lower arch.

In certain embodiments, a method of aligning a virtual model of an upper jaw and a virtual model of a lower jaw in a bite position comprises matching first facial surfaces of a virtual model of a side impression with facial surfaces of the virtual model of the upper jaw and matching second facial surfaces of the virtual model of the side impression with facial surfaces of the virtual model of the lower dental arch. At least a portion of the first facial surfaces of the virtual model of the side impression are the same as the facial surfaces of the virtual model of the upper jaw. At least a portion of the second facial surfaces of the virtual model of the side impression are the same as the facial surfaces of the virtual model of the lower jaw. The aligned virtual model may be stored in a storage device. The method may be computer-implemented.

In certain embodiments, a computer program product comprises computer program code means for executing a method of aligning a virtual model of an upper jaw and a virtual model of a lower jaw in a bite position when the computer program code means are run by an electronic device having computer capabilities. The method comprises matching first facial surfaces of a virtual model of a side impression with facial surfaces of the virtual model of the upper jaw and matching second facial surfaces of the virtual model of the side impression with facial surfaces of the virtual model of the lower jaw. At least a portion of the first facial surfaces of the virtual model of the side impression are the same as the facial surfaces of the virtual model of the upper jaw. At least a portion of the second facial surfaces of the virtual model of the side impression are the same as the facial surfaces of the virtual model of the lower jaw.

In certain embodiments, a computer-readable physical storage device that stores instructions executable by at least one processing device comprises instructions that, when executed, cause the processing device to perform a method of aligning a virtual model of an upper jaw and a virtual model of a lower jaw in a bite position. The method comprises matching first facial surfaces of a virtual model of a side impression with facial surfaces of the virtual model of the upper jaw and matching second facial surfaces of the virtual model of the side impression with facial surfaces of the virtual model of the lower jaw. At least a portion of the first facial surfaces of the virtual model of the side impression are the same as the facial surfaces of the virtual model of the upper jaw. At least a portion of the second facial surfaces of the virtual model of the side impression are the same as the facial surfaces of the virtual model of the lower jaw.

In certain embodiments, a computing system comprises at least one unit configured to align a virtual model of an upper jaw and a virtual model of a lower jaw in a bite position by matching first facial surfaces of a virtual model of a side impression with facial surfaces of the virtual model of the upper jaw and matching second facial surfaces of the virtual model of the side impression with facial surfaces of the virtual model of the lower jaw. At least a portion of the first facial surfaces of the virtual model of the side impression are the same as the facial surfaces of the virtual model of the upper jaw. At least a portion of the second facial surfaces of the virtual model of the side impression are the same as the facial surfaces of the virtual model of the lower jaw.

In certain embodiments, a computer comprises hardware configured to execute a program for aligning a virtual model of an upper jaw and a virtual model of a lower jaw in a bite position by matching facial surfaces of a virtual model of a side impression with facial surfaces of the virtual model of the upper dental arch and with facial surfaces of the virtual model of the lower dental arch.

In certain embodiments, a method comprises forming a side impression comprising facial surfaces of a portion of an upper jaw and facial surfaces of a portion of a lower jaw. The side impression is substantially free of occlusal surfaces of the upper jaw and the lower jaw.

In certain embodiments, a method comprises scanning a side impression comprising facial surfaces of at least a portion of an upper jaw and facial surfaces of at least a portion of a lower jaw.

In certain embodiments, a method comprises aligning a virtual model of an upper jaw and a virtual model of a lower jaw in a bite position using only three sets of scanned impression data. In such an embodiment, the three sets of scanned impression data can correspond to an impression of at least a portion of the lower jaw, an impression of a least a portion of the upper jaw, and a side impression comprising facial surfaces of a portion of an upper jaw and facial surfaces of a portion of a lower jaw. The side impression can be substantially free of occlusive surfaces and/or occlusal of the upper jaw and the lower jaw.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the invention disclosed herein are described below with reference to the drawings of certain embodiments, which are intended to illustrate certain embodiments and not to limit the invention.

FIG. 3Bi is an example cross-section taken along the line B-B of FIG. 3.

FIG. 3Bii is another example cross-section taken along the line B-B of FIG. 3.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Figure 1A:
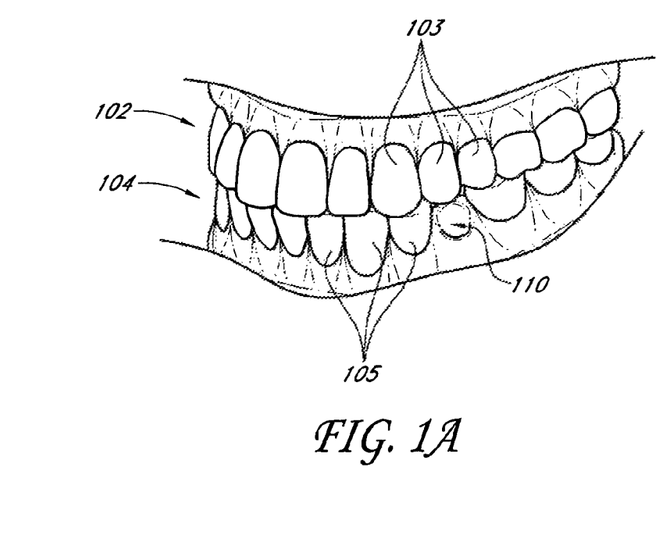
FIG. 1A is a perspective view of example of upper and lower jaws in a bite position.
Figure 1B:
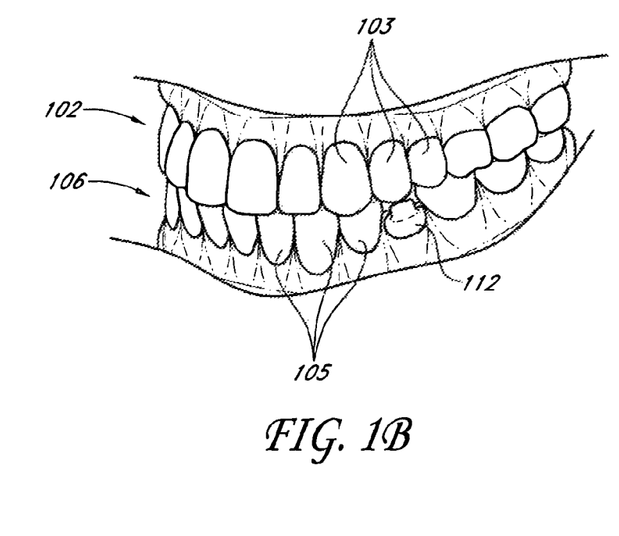
FIG. 1B is a perspective view of another example of upper and lower jaws in a bite position.

FIGS. 1A and 1B are perspective views of examples of an upper jaw 102 and lower jaws 104, 106. The illustrated upper jaw 102 comprises an upper dental arch including maxillary teeth 103, although a completely edentulous upper jaw is also possible. The illustrated lower jaws 104, 106 comprise lower dental arches including mandibular teeth 105, although a completely edentulous lower jaw is also possible. The upper jaw and/or the lower jaw may include prosthesis (e.g., impression coping, coping, crown, inlay, overlay, veneer, bridge, framework) and/or markers (e.g., an alignment feature attached to a facial surface of at least one tooth or prosthesis). Each maxillary tooth 103 comprises a crown portion below a gingival boundary and a root portion above the gingival boundary and each mandibular tooth 105 comprises a crown portion above a gingival boundary and a root portion below the gingival boundary. The lower jaws 104, 106 each hinge to a skull at a temporal mandibular joint. The upper jaw 102 and the lower jaws 104, 106 are illustrated in the bite position or occlusive position (in which the occlusive surfaces of the upper jaw and the occlusive surfaces of the lower jaw are in contact) in which some maxillary teeth 103 and mandibular teeth 105 overlap each other (e.g., overlapping incisal surfaces) and some teeth in contact (e.g., occlusive surfaces in contact).

The lower jaw 104 of FIG. 1A comprises an edentulous area 110. The edentulous area 110 may be natural (e.g., having never formed) or created (e.g., by extracting the tooth). In certain embodiments, the edentulous area 110 comprises a dental implant (not shown) configured to be osseointegrated with the bone of the lower jaw 104. In some embodiments, the edentulous area 110 comprises an impression coping coupled to a dental implant. In certain such embodiments, the impression coping may comprise facial surfaces that may be used to align the upper jaw 102 and the lower jaw 104.

The lower jaw 106 of FIG. 1B comprises a residual tooth 112. The residual tooth 112 may be natural (e.g., due to chipping) or created (e.g., by grinding a tooth down to a stump in preparation for receiving a prosthesis such as a coping or crown, as illustrated in FIG. 1B, or an inlay, overlay, veneer, bridge, framework, etc.).

The upper jaw 102 and the lower jaws 104, 106 of FIGS. 1A and 1B are provided for illustration purposes only. Those of skill in the art will appreciate that upper and lower jaws may comprise fewer or no teeth, teeth in different orientations (e.g., having different angles, rotations, offsets, heights, widths, etc.), no, additional, or different edentulous areas and/or residual teeth, prostheses (e.g., impression coping, coping, crown, inlay, overlay, veneer, bridge, framework), markers, combinations thereof, and the like. For example, in some embodiments, the upper and lower jaws are completely edentulous.

Figures 2A, 2B, 2C:
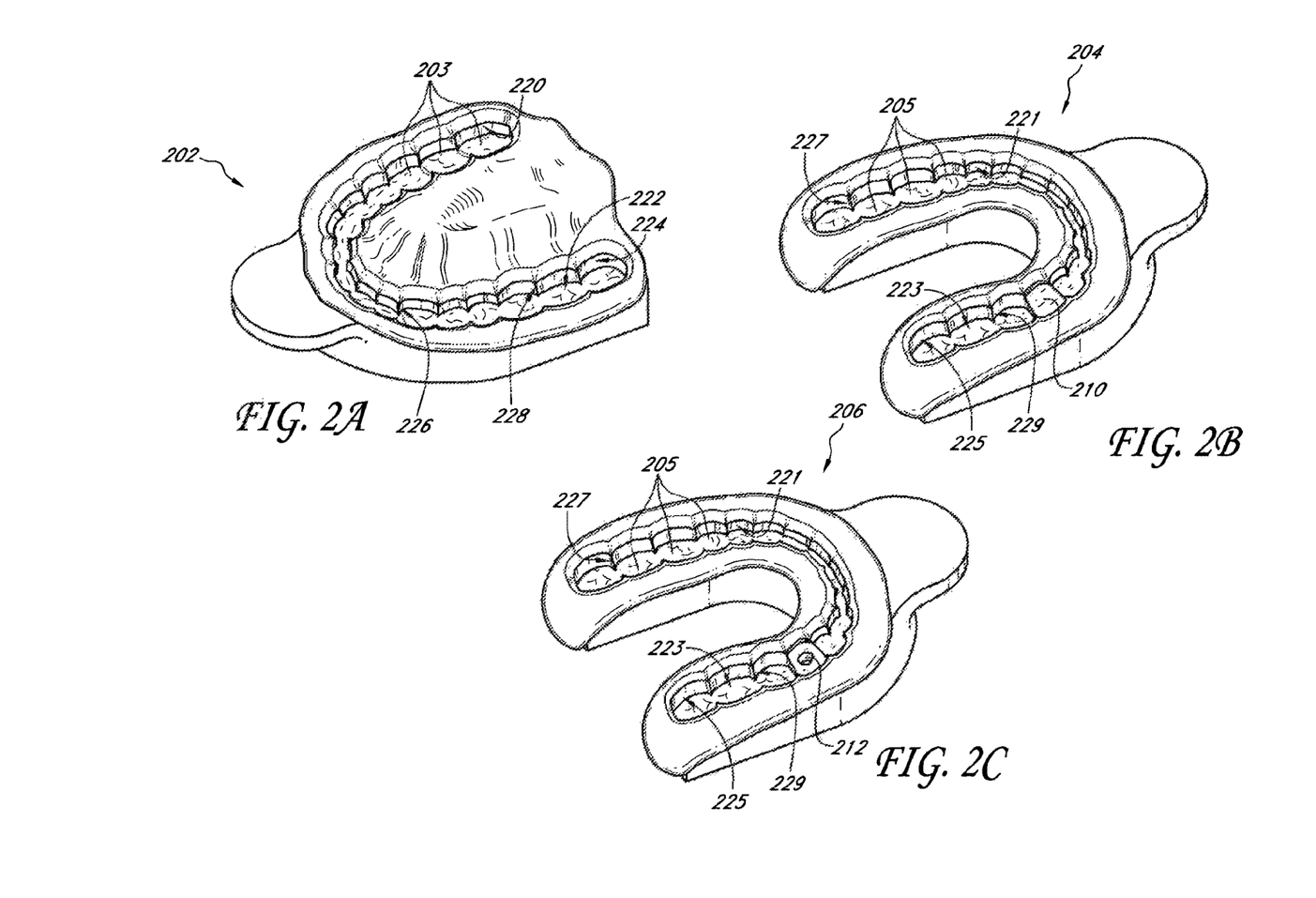
FIG. 2A illustrates an example impression of the upper jaws of FIGS. 1A and 1B.
FIG. 2B illustrates an example impression of the lower jaw of FIG. 1A.
FIG. 2C illustrates an example impression of the lower jaw of FIG. 1B.

FIG. 2A illustrates an example impression 202 of the upper jaw 102 of FIGS. 1A and 1B in impression trays. The impression 202 of the upper jaw 102 includes a recess 203 where the impression material flowed around the plurality of maxillary teeth 103, each maxillary tooth 103 creating a recess portion that together form the recess 203. The recess 203 includes facial surfaces 220, occlusal surfaces 222, and lingual surfaces 224, and possibly fractions of mesial surfaces 226 and/or distal surfaces 228. The occlusal surfaces 222 include occlusive surfaces (i.e., surfaces that make contact with opposing teeth in the bite position). In some embodiments, the impression 202 of the upper jaw 102 includes soft tissue features (e.g., the gingival boundary, gingival surfaces, etc.). In some embodiments, the impression 202 of the upper jaw 102 includes only soft tissue features (e.g., the gingival boundary, gingival surfaces, etc.).

FIGS. 2B and 2C illustrate example impressions 204, 206 of the lower jaws 104, 106 of FIGS. 1A and 1B, respectively. The impressions 204, 206 of the lower jaws 104, 106 each include a recess 205 where the impression material flowed around the plurality of mandibular teeth 105, each mandibular tooth 105 creating a recess portion that together form the recess 205. The recess 205 includes facial surfaces 221, occlusal surfaces 223, and lingual surfaces 225, and possibly fractions of mesial surfaces 227 and/or distal surfaces 229. The occlusal surfaces 223 include occlusive surfaces (i.e., surfaces that make contact with opposing teeth in the bite position). In some embodiments, the impressions 204, 206 of the lower jaws 104, 106 include soft tissue features (e.g., the gingival boundary, gingival surfaces, etc.). In some embodiments, the impressions 204, 206 of the lower jaws 104, 106 include only soft tissue features (e.g., the gingival boundary, gingival surfaces, etc.). In certain embodiments, the impressions of the upper jaw 102 and lower jaws 104, 106 may be formed simultaneously (e.g., by using a triple tray). In some embodiments, the recesses 203, 205 can be divided into one or more sub-recesses, for example when one or several teeth are missing inbetween other teeth of the same jaw.

The impression 204 of the lower jaw 204 illustrated in FIG. 2B does not include a recess portion in the edentulous area 110 of the lower jaw 104, but may include an impression of soft tissue features such as the illustrated shallow recess 210. In some embodiments in which the edentulous area 110 comprises an implant and a healing abutment, the impression 204 of the lower jaw 104 may include an impression of the healing abutment. In certain such embodiments, the implant may be attached to an implant position locator or impression coping and the impression 204 of the lower jaw 104 may include an impression of the position locator or impression coping. The impression 206 of the lower jaw 106 illustrated in FIG. 2C includes an indentation 212 where the impression material flowed around the residual tooth 112 of the lower jaw 106.

In some embodiments, the impression 202 of the upper jaw 102 only comprises a portion of the upper jaw 102 and the impression 204, 206 of the lower jaw 104, 106 only comprises a portion of the lower jaw 104, 106. Certain such partial impressions may have advantages such as, for example, less impression material used, less patient discomfort during forming the impression, less time and material used for making physical models therefrom, less imaging or scan time upon conversion to a virtual model, and less data for a virtual model, possibly leading to faster manipulation of the virtual model. In certain such embodiments, the impressions include a site where dental rehabilitation is to take place.

As an example, in an embodiment in which one or more prostheses (e.g., an abutment and a coping, crown, inlay, overlay, veneer, bridge, framework, etc.) is to be fabricated for the edentulous area 110, the impression 202 of the upper jaw 102 and the impression 204 of the lower jaw 104 may comprise an impression of facial surfaces adjacent or near to the edentulous area 110. In certain such embodiments, the impression 202 of the upper jaw 102 may comprise an impression of at least a portion of at least one maxillary tooth 103 proximate to the edentulous area 110 and the impression 204 of the lower jaw 104 may comprise an impression of at least a portion of at least one mandibular tooth 105 proximate to the edentulous area 110. In certain such embodiments, the impression 204 of the lower jaw 104 may further comprise the shallow recess 210, which is an example impression of an edentulous area 110. In certain other such embodiments, the impression 204 of the lower jaw 104 may comprise a recess portion formed by a mandibular tooth 105 mesial to the edentulous area 110 and a recess portion formed by a mandibular tooth 105 distal to the edentulous area 110, and the impression 202 of the upper jaw 102 may comprise a recess portion formed by a maxillary tooth 103 opposing the edentulous area 110 or a recess formed by maxillary teeth 103 opposing the edentulous area 110, the mesial mandibular tooth 105, and the distal mandibular tooth 105. In certain such embodiments, the impression 204 of the lower jaw 104 may further comprise the shallow recess 210, which is an example impression of an edentulous area 110.

In some embodiments, the impression 202 of the upper jaw 102 comprises the entire upper jaw 102 and the impression 204 of the lower jaw 104 comprises the entire lower jaw 104. In certain such embodiments, the side impression, described herein, may comprise an impression of facial surfaces adjacent to or near the edentulous area 110. In certain such embodiments, the side impression may comprise an impression of at least a portion of at least one maxillary tooth 103 proximate to the edentulous area 110 and an impression of at least a portion of at least one mandibular tooth 105 proximate to the edentulous area 110. In certain such embodiments, the side impression may further comprise an impression of the edentulous area 110. In certain other such embodiments, the side impression may comprise facial surfaces formed by a mandibular tooth 105 mesial to the edentulous area 110, facial surfaces formed by a mandibular tooth 105 distal to the edentulous area 110, facial surfaces formed by a maxillary tooth 103 opposing the edentulous area 110 or facial surfaces formed by maxillary teeth 103 opposing the edentulous area 110, the mesial mandibular tooth 105, and the distal mandibular tooth 105. In certain such embodiments, the side impression may further comprise an impression of the edentulous area 110.

As another example, in an embodiment in which one or more prostheses (e.g., a coping, crown, inlay, overlay, veneer, bridge, framework, etc.) is to be fabricated for the residual tooth 112, the impression 202 of the upper jaw 102 and the impression 206 of the lower jaw 104 may comprise an impression of facial surfaces adjacent to the residual tooth 112. In certain such embodiments, the impression 202 of the upper jaw 102 may comprise an impression of at least a portion of at least one maxillary tooth 103 proximate to the residual tooth 112 and the impression 206 of the lower jaw 106 may comprise an impression of at least a portion of at least one mandibular tooth 105 proximate to the residual tooth 112. In certain such embodiments, the impression 206 of the lower jaw 106 may comprise the indentation 212. In certain other such embodiments, the impression 206 of the lower jaw 106 may comprise a recess portion formed by a mandibular tooth 105 mesial to the residual tooth 112 and a recess portion formed by a mandibular tooth 105 distal to the residual tooth 112, and the impression 202 of the upper jaw may comprise a recess portion formed by a maxillary tooth 103 opposing the residual tooth 112 or a recesses formed by maxillary teeth 103 opposing the residual tooth 112, the mesial mandibular tooth 105, and the distal mandibular tooth 105. In certain such embodiments, the impression 206 of the lower jaw 106 may comprise the indentation 212.

In some embodiments, the impression 202 of the upper jaw 102 comprises the entire upper jaw 102 and the impression 206 of the lower jaw 106 comprises the entire lower jaw 106. In certain such embodiments, the side impression, described herein, may comprise an impression of facial surfaces adjacent to the residual tooth 112. In certain such embodiments, the side impression may comprise an impression of at least a portion of at least one maxillary tooth 103 proximate to the residual tooth and an impression of at least a portion of at least one mandibular tooth 105 proximate to the residual tooth 112. In certain such embodiments, the side impression may further comprise an impression of the residual tooth 112. In certain other such embodiments, the side impression may comprise facial surfaces formed by a mandibular tooth 105 mesial to the residual tooth 112, facial surfaces formed by a mandibular tooth 105 distal to the edentulous area 110, facial surfaces formed by a maxillary tooth 103 opposing the residual tooth 112 or facial surfaces formed by maxillary teeth 103 opposing the residual tooth 112, the mesial mandibular tooth 105, and the distal mandibular tooth 105. In certain such embodiments, the side impression may further comprise an impression of the residual tooth 112.

In some embodiments, the side impression does not include a site where dental rehabilitation is to take place (e.g., the side impression does not comprise an impression of an edentulous area 110 or an impression of a residual tooth 112). In certain such embodiments, areas of the dentition that may be more difficult to capture (e.g., sensitive areas or less-easily accessed areas) may be avoided. In some embodiments in which the side impression does not include the site where dental rehabilitation is to take place, a wider scan area is used in order to improve accuracy of the alignment, thereby improving accuracy at the site and opposite to the site. The wider scan area can, e.g., comprise at least a portion of a tooth and adjacent soft tissue features, such as soft tissue boundary and/or soft tissue.

Figure 3:
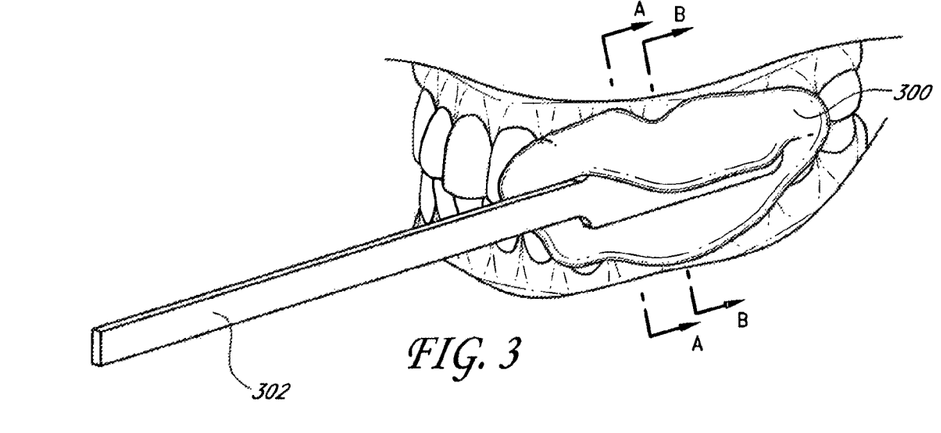
FIG. 3 illustrates an example embodiment of forming an side impression of upper and lower jaws in the bite position.

FIG. 3 illustrates an example embodiment of forming a side impression of upper and lower jaws in the bite position. With the patient in occlusive position, impression material 300, which may be held by an applicator 302, is applied to the facial surfaces of the upper and lower jaws. In some embodiments, the impression material 300 contacts at least a portion of a maxillary tooth 103 and at least a portion of a mandibular tooth 105. In some embodiments, the impression material 300 contacts at least a portion of a plurality of maxillary teeth 103 and/or at least a portion of a plurality of mandibular teeth 105. In some embodiments, the impression material 300 contacts the entire facial surface of a maxillary tooth 103 and/or the entire facial surface of a mandibular tooth 105. In some embodiments, the impression material 300 contacts the entire facial surface of a plurality of maxillary teeth 103 and/or the entire facial surface of a plurality of mandibular teeth 105. In some embodiments, the impression material 300 contacts the entire facial surface of a maxillary tooth 103 including soft tissue and/or the entire facial surface of a mandibular tooth 105 including soft tissue. In some embodiments, the impression material 300 contacts the entire facial surface of a plurality of maxillary teeth 103 including soft tissue and/or the entire facial surface of a plurality of mandibular teeth 105 including soft tissue. In some embodiments, the impression material 300 contacts the entire facial surface of a plurality of maxillary teeth 103 including only soft tissue and/or the entire facial surface of a plurality of mandibular teeth 105 including only soft tissue. In embodiments in which the maxillary tooth 103 and the mandibular tooth 105 comprise posterior teeth (premolars and/or molars), the side impression includes buccal surfaces. In embodiments in which the maxillary tooth 103 and the mandibular tooth 105 comprise anterior teeth (incisors and/or cuspids), the side impression includes labial surfaces. In certain embodiments, the impression material 300 is applied to at least one quadrant and includes the entire facial surfaces of the teeth in that quadrant.

In the impression formation illustrated in FIG. 3, the impression material 300 is substantially free of occlusive surfaces because the impression material 300 was applied with the upper jaw and the lower jaw in the bite position. That is, the patient did not bite down on the impression material 300, such that, while the impression material 300 may squeeze between occlusal surfaces and mesial/distal surfaces where there is not contact, the impression material 300 cannot squeeze between occlusive surfaces. In certain alternative embodiments, forming a side impression may include occlusive surfaces by causing the patient to bite down on the impression material 300 during application.

Figure 3A:
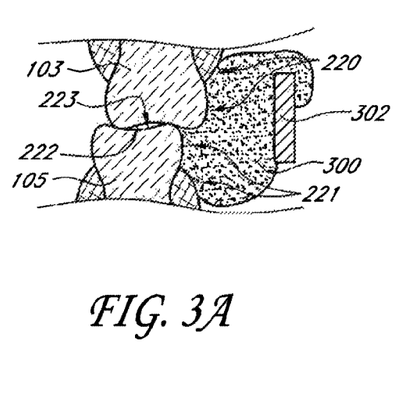
FIG. 3A is an example cross-section taken along the line A-A of FIG. 3.

FIG. 3A is an example cross-section taken along the line A-A of FIG. 3. The impression material 300 abuts the facial surfaces 220 of the upper jaw 102 (as illustrated, the facial surfaces 220 of the maxillary tooth 103) and the facial surfaces 221 of the lower jaw 104, 406 (as illustrated, the facial surfaces 221 of the mandibular tooth 105) such that the resulting side impression comprises an impression of the facial surfaces 220 of the maxillary tooth 103 and an impression of the facial surfaces 221 the mandibular tooth 105. The impression material 300 does not penetrate the occlusive surfaces of the occlusal surfaces 222, 223. In some embodiments, the impression material 300 abuts the soft tissue above the maxillary tooth 103 and/or below the mandibular tooth 105 such that the resulting side impression comprises an impression of the soft tissue of the upper jaw 102 and/or an impression of the soft tissue of the lower jaw 104. In the illustrated embodiment, the impression material 300 captures portions of the occlusal surfaces 222 of the maxillary tooth 103, for example in the area prior to contact with the mandibular tooth 105, such that the side impression is substantially free of occlusal surfaces and is substantially free (e.g., completely free) of occlusive surfaces. In embodiments, the impression is free from areas of opposing teeth that are in contact in the bite position.

FIG. 3Bi is an example cross-section taken along the line B-B of FIG. 3. The impression material 300 abuts the facial surfaces 220 of the upper jaw 102 (as illustrated, the facial surfaces 220 of the maxillary tooth 103) and the facial surfaces 221 of the lower jaw 104 (as illustrated, the soft tissue of the edentulous area 110) such that the resulting side impression comprises an impression of the facial surfaces 220 of the maxillary tooth 103 and an impression of the edentulous area 110. There are no occlusive surfaces because the maxillary tooth 103 does not contact a mandibular tooth, so the impression material 300 can penetrate the occlusal surfaces 222 of the maxillary tooth 103. In some embodiments, the impression material 300 abuts the soft tissue above the maxillary tooth 103 such that the resulting side impression comprises an impression of the soft tissue of the upper jaw 102 and an impression of the soft tissue of the edentulous area 110 of the lower jaw 104. In embodiments in which the edentulous area 110 comprises a dental implant and an impression coping, the impression material 300 may abut the facial surfaces 220 of the upper jaw 102 (e.g., facial surfaces 220 of a maxillary tooth 103) and the facial surfaces 221 of the lower jaw 104 (e.g., facial surfaces 221 of the impression coping) such that the resulting side impression comprises an impression of the facial surfaces 220 of the maxillary tooth 103 and an impression of the facial surfaces 221 of the impression coping. In the illustrated embodiment, the impression material 300 captures portions of the occlusal surfaces 222 of the maxillary tooth 103. In certain embodiments, less impression material 300 may be used such that the side impression is substantially free of occlusal surfaces and is substantially free (e.g., completely free) of occlusive surfaces. In embodiments, the impression is free from areas of opposing teeth that are in contact in the bite position.

FIG. 3Bii is another example cross-section taken along the line B-B of FIG. 3. The impression material 300 abuts the facial surfaces 220 of the upper jaw 102 (as illustrated, the facial surfaces 220 of the maxillary tooth 103) and the facial surfaces 221 of the lower jaw 106 (as illustrated, the facial surfaces 220 of the residual tooth 112) such that the resulting side impression comprises an impression of the facial surfaces 220 of the maxillary tooth 103 and an impression of the facial surfaces 221 of the residual tooth 112. In the illustrated embodiment, there are no occlusive surfaces because the maxillary tooth 103 does not contact the residual tooth 112, so the impression material 300 can penetrate the occlusal surfaces 222 of the maxillary tooth 103. In some embodiments, the impression material 300 abuts the soft tissue above the maxillary tooth 103 and/or below the residual tooth 112 such that the resulting side impression comprises an impression of the soft tissue of the upper jaw 102 and/or an impression of the soft tissue of the lower jaw 104. In the illustrated embodiment, the impression material 300 captures portions of the occlusal surfaces 222 of the maxillary tooth 103. In certain embodiments, less impression material 300 may be used such that the side impression is substantially free of occlusal surfaces and is substantially free (e.g., completely free) of occlusive surfaces. In embodiments, the impression is free from areas of opposing teeth that are in contact in the bite position.

Figure 4A:
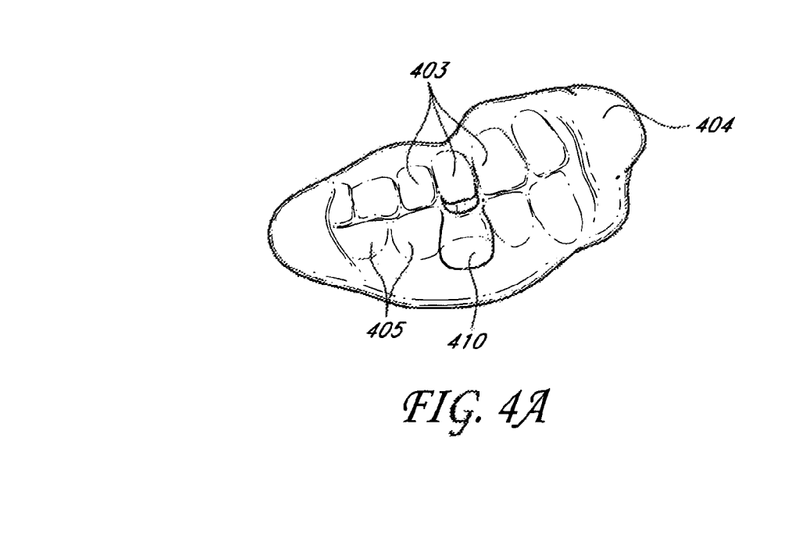
FIG. 4A illustrates an example embodiment of a side impression of the upper and lower jaws of FIG. 1A.
Figure 4B:
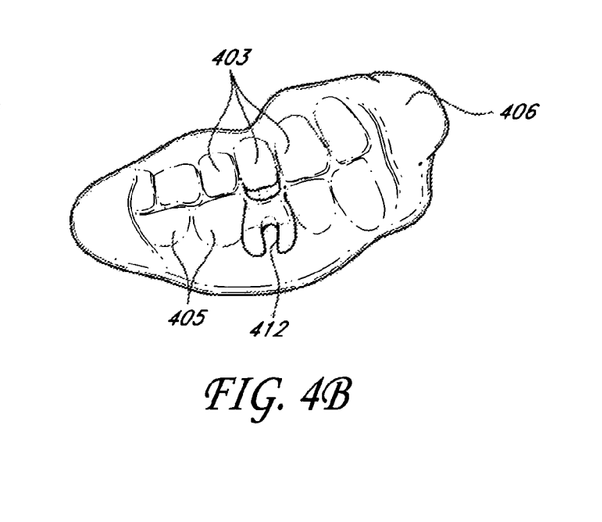
FIG. 4B illustrates an example embodiment of a side impression of the upper and lower jaws of FIG. 1B.

FIG. 4A illustrates an example embodiment of a side impression 404 of facial surfaces of the upper jaw 102 and of facial surfaces the lower jaw 104 of FIG. 1A. FIG. 4B illustrates an example embodiment of a side impression 406 of facial surfaces of the upper jaw 102 and of facial surfaces the lower jaw 106 of FIG. 1B. The side impressions 404, 406 each include recesses 403 where the impression material 300 flowed around the facial surfaces 220 of a plurality of maxillary teeth 103 and recesses 405 where the impression material 300 flowed around the facial surfaces 221 of a plurality of mandibular teeth 105. The side impression 404 also includes a projection 410 where the impression material 300 flowed into the edentulous area 110. Although the projection 410 may include information about the occlusal surfaces 222 of the maxillary tooth 103 above the edentulous area 110, the side impression 404 is substantially free of occlusive surfaces because the impression material 300 was applied while the patient was already in the bite position. The side impression 406 also includes a projection 412 where the impression material 300 flowed around the residual tooth 112. Although the projection 412 may include information about the occlusal surfaces 222 of the maxillary tooth 103 above the residual tooth 112, the side impression 406 is substantially free of occlusive surfaces because the impression material 300 was applied while the patient was already in the bite position. Those skilled in the art will appreciate that the side impressions 404, 406 may also include information about the mesial surfaces 226, 227, distal surfaces 228, 229, and lingual surfaces 224, 225 where the impression material 300 flowed through gaps between the teeth 103, 105.

In certain embodiments, the impression material 300 for the side impression is applied proximate to a site where dental rehabilitation is to take place. For example, in an embodiment where one or more prostheses (e.g., an abutment and a coping, crown, inlay, overlay, veneer, bridge, framework, etc.) is to be fabricated for the edentulous area 110, the side impression 404 may comprise an impression of at least a portion of a maxillary tooth 103 proximate to the edentulous area 110 and an impression of at least a portion of a mandibular tooth 105 proximate to the edentulous area 110. In certain such embodiments, the side impression 404 may further comprise the edentulous area 110. In certain such embodiments, the side impression 404 may comprise impressions of a mandibular tooth 105 mesial to the edentulous area 110, a mandibular tooth 105 distal to the edentulous area 110, and the maxillary teeth 103 opposing each of the edentulous area 110, the mesial mandibular tooth 105, and the distal mandibular tooth 105. For another example, in an embodiment where one or more prostheses (e.g., a coping, crown, inlay, overlay, veneer, bridge, framework, etc.) is to be fabricated for the residual tooth 112, the side impression 406 may comprise an impression of at least a portion of a maxillary tooth 103 proximate to the residual tooth 112 and an impression of at least a portion of a mandibular tooth 105 proximate to the residual tooth 112. In certain such embodiments, the side impression 406 may further comprise the residual tooth 112. In certain such embodiments, the side impression 406 may comprise impressions of a mandibular tooth 105 mesial to the residual tooth 112, a mandibular tooth 105 distal to the residual tooth 112, and the maxillary teeth 103 opposing each of the residual tooth 112, the mesial mandibular tooth 105, and the distal mandibular tooth 105.

The accuracy of the alignment of the virtual model of the upper jaw and the virtual model of the lower jaw in the bite position is generally most accurate at the position where matching takes place. In embodiments in which the aligned virtual model is used to create a prosthesis, accuracy is most desirable at the site where dental rehabilitation is to take place (e.g., at an edentulous area, at a residual tooth). In some embodiments in which the aligned virtual model is used to create a prosthesis, matching is at a position proximate to, and preferably including, the site where dental rehabilitation is to take place in order to increase the accuracy of the alignment of the upper jaw and the virtual model of the lower jaw in the bite position where accuracy is most desired.

In a side impression, the facial surfaces used for matching are non-opposing and generally face in the same direction. This allows the facial surfaces to be scanned at the same time (e.g., in a single scan). By contrast, in a bite impression, the occlusal surfaces used for matching are opposing each other, which requires the occlusal surfaces to be scanned at two different times (e.g., in two different scans). In certain embodiments, a side impression comprises facial surfaces and is substantially free of occlusive surfaces. By contrast, a bite impression comprises occlusal and occlusive surfaces and is substantially free of facial surfaces. In certain embodiments, a side impression comprises a thickness greater than about 3 mm from facial surfaces because the impression material is only limited by the distance between the facial surfaces of the upper jaw and the lower jaw and the patient's cheek. This thickness can provide an impression in which the facial surfaces used for matching are not prone to deformation. By contrast, a bite impression is thin and weak at the occlusal surfaces used for matching because the space between the upper jaw and the lower jaw in the bite position is generally very small and occlusive surfaces can cause perforations. This thinness can cause the bite impression to be prone to deformation at the surfaces that are used for matching, which can lead to inaccurate alignment of the virtual model of the upper jaw and the virtual model of the lower jaw.

In certain embodiments, the material of the impressions 202, 204, 206, 304, 306 is the same. In some embodiments, impression material may be selected based on a later process. For example, in embodiments in which negative impressions will be imaged, the impression material may have properties suitable for such imaging (e.g., Impregum™ or Impregum F™, both available from 3M of St. Paul, Minn., for laser imaging). For another example, in embodiments in which a stone model will be created, the impression material may have properties suitable for such casting.

Three impressions, the side impression, the impression of the upper jaw, and the impression of the lower jaw, are converted into virtual or digital models, for example by laser scanning or white light scanning. The result is three independent data files: a data file for the side impression that is a virtual or digital model of the side impression, a data file for the impression of the upper jaw that is a virtual or digital model of the upper jaw, and a data file for the impression of the lower jaw that is a virtual or digital model of the lower jaw. The "negative" impressions may be scanned, a "positive" physical model formed from the impressions may be scanned, or a combination thereof. The impressions or physical models may each be scanned with destructive methods, non-destructive methods, or a combination thereof.

The virtual model of the side impression comprises a model of facial surfaces 220 of at least a portion of the upper jaw (e.g., a maxillary tooth, soft tissue, a residual tooth, a prosthesis, an edentulous area, an impression coping, etc.) and facial surfaces 221 of at least a portion of the lower jaw (e.g., a mandibular tooth, soft tissue, a residual tooth, a prosthesis, an edentulous area, an impression coping, etc.). In embodiments in which the impression material 300 contacts at least a portion of a plurality of maxillary teeth 103 and at least a portion of a plurality of mandibular teeth 105, the virtual model of the side impression comprises a model of facial surfaces 220 of at least a portion of the plurality of maxillary teeth 103 and facial surfaces 221 at least a portion of the plurality of mandibular teeth 105. In embodiments in which the impression material 300 contacts the entire facial surface 220 of a maxillary tooth 103 and the entire facial surface 221 of a mandibular tooth 105, the virtual model of the side impression comprises a model of the entire facial surface of the maxillary tooth 103 and the entire facial surface of the mandibular tooth 105. In embodiments in which the impression material 300 contacts the entire facial surface 220 of a plurality of maxillary teeth 103 and the entire facial surface 221 of a plurality of mandibular teeth 105, the virtual model of the side impression comprises a model of the entire facial surface 220 of the plurality of maxillary teeth 103 and the entire facial surface 221 of the plurality of mandibular teeth 105. In embodiments in which the maxillary tooth 103 and the mandibular tooth 105 comprise posterior teeth (premolars and/or molars), the virtual model of the side impression includes a model of buccal surfaces. In embodiments in which the maxillary tooth 103 and the mandibular tooth 105 comprise anterior teeth (incisors and/or cuspids), the virtual model of the side impression includes a model of labial surfaces. In certain embodiments, the virtual model of the side impression comprises a model of the maxillary teeth 103 and the mandibular teeth 105 of at least one quadrant and includes the entire facial surfaces 220, 221 of the teeth 103, 105 in that quadrant. In embodiments in which the side impression is formed as illustrated in FIG. 3, the virtual model of the side impression is substantially free of occlusive surfaces.

In embodiments in which the side impression comprises an impression of a site where dental rehabilitation is to take place, such as a site prepared to receive a prosthesis (e.g., the edentulous area 110, the residual tooth 112), the virtual model of the side impression comprises a model of the site prepared to receive the prosthesis. In certain such embodiments, the site comprises an edentulous area 100 comprising at least one implant and/or at least one residual tooth 112. For example, in an embodiment where one or more prostheses (e.g., an abutment and a coping, crown, inlay, overlay, veneer, bridge, framework, etc.) is to be fabricated for the edentulous area 110, the virtual model of the side impression may comprise a model of at least a portion of a maxillary tooth 103 proximate to the edentulous area 110 and a model of at least a portion of a mandibular tooth 105 proximate to the edentulous area 110. In certain such embodiments, the virtual model of the side impression may further comprise a model of the edentulous area 110. In certain such embodiments, the virtual model of the side impression may comprise a model of a mandibular tooth 105 mesial to the edentulous area 110, a model of a mandibular tooth 105 distal to the edentulous area 110, and a model of the maxillary teeth 103 opposing each of the edentulous area 110, the mesial mandibular tooth 105, and the distal mandibular tooth 105. For another example, in an embodiment where one or more prostheses (e.g., a coping, crown, inlay, overlay, veneer, bridge, framework, etc.) is to be fabricated for the residual tooth 112, the virtual model of the side impression may comprise a model of at least a portion of a maxillary tooth 103 proximate to the residual tooth 112 and a model of at least a portion of a mandibular tooth 105 proximate to the residual tooth 112. In certain such embodiments, the virtual model of the side impression may further comprise a model of the residual tooth 112. In certain such embodiments, the virtual model of the side impression may comprise a model of a mandibular tooth 105 mesial to the residual tooth 112, a model of a mandibular tooth 105 distal to the residual tooth 112, and a model of the maxillary teeth 103 opposing each of the residual tooth 112, the mesial mandibular tooth 105, and the distal mandibular tooth 105. For at least the reasons described above, in some embodiments in which the aligned virtual model is used to create a prosthesis, matching is at a position proximate to, and preferably including, the site where dental rehabilitation is to take place in order to increase the accuracy of the alignment of the upper jaw and the virtual model of the lower jaw in the bite position where accuracy is most desired.

In some embodiments, a virtual model of an upper jaw and a virtual model of a lower jaw are aligned in a bite position by matching facial surfaces of the upper jaw (e.g., facial surfaces of at least a portion of a maxillary tooth) with facial surfaces of a virtual model of a side impression (e.g., the facial surfaces of the portion of the maxillary tooth) and by matching facial surfaces of the lower jaw (e.g., facial surfaces of at least a portion of a mandibular tooth) with facial surfaces of the virtual model of the side impression (e.g., the facial surfaces of the portion of the mandibular tooth). That is, the same surfaces (e.g., facial surfaces) on the upper jaw are represented by portions of the virtual model of the upper jaw and portions of the virtual model of the side impression. In a similar manner, the same surfaces (e.g., facial surfaces) on the lower jaw are represented by portions of the virtual model of the lower jaw and portions of the virtual model of the side impression. The virtual upper and lower jaw can be aligned in their bite position by matching the common surfaces in the virtual models of the upper and lower jaw with their respective common surfaces in the virtual side impression. Although facial surfaces may include fossae, pits, soft tissue, crevasses, etc., facial surfaces are generally smooth and thus surface matching can have fewer complications than occlusal surface matching. The matched surfaces are used to orient each of the virtual model of the upper jaw and the virtual model of the lower jaw with respect to the virtual model of the side impression, thereby aligning the virtual model of the upper jaw and the virtual model of the lower jaw in the bite position. In certain embodiments, matching facial surfaces may be performed using Geomagic Qualify, available from Geomagic, Inc. of Research Triangle Part, N.C. In some embodiments, matching facial surfaces includes user input (e.g., selecting portions of the facial surfaces to be matched, such as the central portion of facial surfaces of teeth). In certain embodiments, matching facial surfaces may be fully automated such that the technician scans the three impressions and then views on a display a virtual model of the upper and lower jaws aligned in the bite position.

In some embodiments, the virtual model of the upper impression and the virtual model of the lower impression are aligned in the bite position by using geometric surface matching to match surfaces (e.g., facial surfaces) with the virtual model of the side impression. Facial surfaces of the upper jaw of the virtual model of the bite impression (e.g., facial surfaces of at least a portion of a maxillary tooth) and facial surfaces of the upper jaw of the virtual model of the upper arch (e.g., the facial surfaces of the portion of the maxillary tooth) are geometrically matched. Facial surfaces of the lower jaw of the virtual model of the bite impression (e.g., facial surfaces of at least a portion of a mandibular tooth) and facial surfaces of the virtual model of the lower jaw (e.g., the facial surfaces of the portion of the mandibular tooth) are geometrically matched. In some embodiments, geometric matching includes iterating the following steps at least one time: select points on the facial surfaces of the virtual model of the bite impression (e.g., the points being evenly distributed across the facial surfaces, the points being clustered on a certain portion of the facial surfaces, the points spanning facial surfaces of hard tissue and soft tissue, etc.); remove any other points; optionally remove noisy data (e.g., by filtering based on distance distribution); compute the closest points on the virtual models of the upper and lower jaws; compute a transformation that matches the selected points to the facial surfaces of the virtual models of the upper and lower jaws; and minimizing the sum of squared distances between corresponding points. In some embodiments, geometric matching includes iterating the following steps at least one time: select points on the facial surfaces of the virtual models of the upper and lower jaws (e.g., the points being evenly distributed across the facial surfaces, the points being clustered on a certain portion of the facial surfaces, the points spanning facial surfaces of hard tissue and soft tissue, etc.); remove any other points; optionally remove noisy data (e.g., by filtering based on distance distribution); compute the closest points on the virtual model of the bite impression; compute a transformation that matches the selected points to the facial surfaces of the virtual model of the bite impression; and minimizing the sum of squared distances between corresponding points. Combinations are also possible (e.g., selecting points on the facial surfaces of the virtual model of the bite impression corresponding to the upper jaw and selecting point on the facial surfaces of the virtual model of the lower jaw, selecting points on the facial surfaces of the virtual model of the bite impression corresponding to the lower jaw and selecting point on the facial surfaces of the virtual model of the upper jaw, etc.). If the result is acceptable, the process may complete or repeat (e.g., to refine the matching). If the result is not acceptable the process may be repeated for at least one more iteration. Different points on the facial surfaces of the selected virtual model or models may be used, or other modifications may be made (e.g., adding random transformations). If the number of iterations reaches a limit without producing an acceptable result, the program may alert a technician that there may be a problem with the impressions or the models of the virtual impression.

After alignment, the technician can then utilize the aligned virtual model, for example, to design orthodontic appliances, to plan or adjust movement of teeth with orthodontic appliances, and to model dental prostheses (e.g., abutments, copings, crowns, inlays, overlays, veneers, bridges, frameworks, etc.).

Figure 5A:
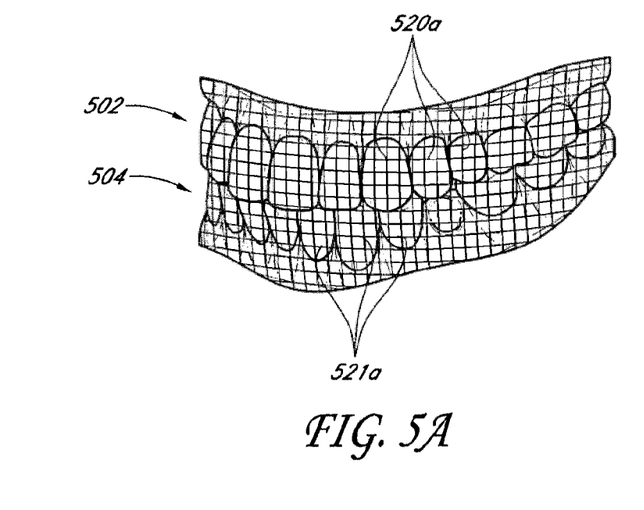
FIG. 5A is an example embodiment of a display of a virtual model of an upper jaw and a virtual model of a lower jaw aligned in the bite position.
Figure 5B:
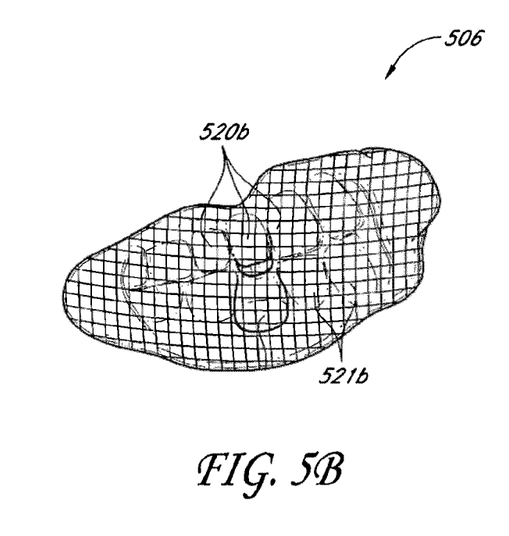
FIG. 5B is an example embodiment of a display of a virtual model of a side impression.

FIG. 5A is an example embodiment of a display of a virtual model of an upper jaw 502 and a virtual model of a lower jaw 504 aligned in the bite position. FIG. 5B is an example embodiment of a display of a virtual model of a side impression 506. Such images can be obtained through scanning the side, upper and lower jaw impressions described above. The scanned data can then be displayed upon a computer display after suitable processing. In one embodiment, the displayed data can be used by a user to aid or adjust matching or alignment of the virtual images of the lower and upper jaw in the bite position. In some embodiments, only the display of the virtual models of the upper jaw and lower jaw 502, 504 are shown to the user. In some embodiments, the matching described above provides an initial bite position between the virtual images of the upper and lower jaws that can be automatically and/or manually adjusted thereafter based upon user input and/or calculated contact points between occlusive surfaces.

Accordingly, with reference to FIGS. 5A and 5B, a method of aligning a virtual model of an upper jaw (502) and a virtual model of a lower jaw (504) in a bite position can comprise matching first facial surfaces (520*b*) of a virtual model of a side impression (506) with facial surfaces (520*a*) of the virtual model of the upper jaw (502), at least a portion of the first facial surfaces (520*b*) of the virtual model of the side impression (506) being the same as the facial surfaces (520*a*) of the virtual model of the upper jaw (502), and matching second facial surfaces (521*b*) of the virtual model of the side impression (506) with facial surfaces (521*a*) of the virtual model of the lower jaw (504), at least a portion of the second facial surfaces (521*b*) of the virtual model of the side impression (506) being the same as the facial surfaces (521*a*) of the virtual model of the lower jaw (504).

Figure 6A:
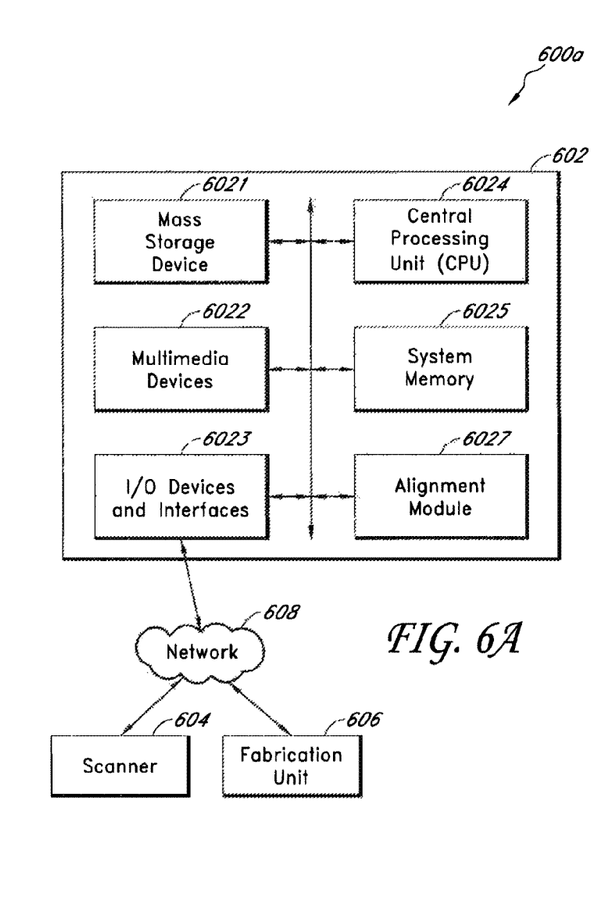
FIG. 6A is a schematic block diagram of an example dental modeling system.
Figure 6B:
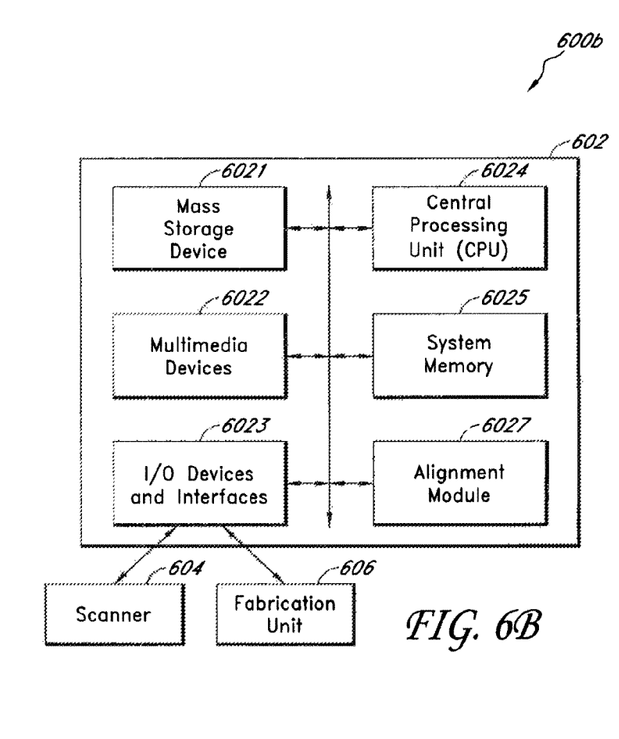
FIG. 6B is a schematic block diagram of another example dental modeling system.

In some embodiments, the methods and systems described herein may take the form of or be executed on a computing system (e.g., a computer) comprising at least one unit configured to align a virtual model of an upper jaw and a virtual model of a lower jaw in a bite position by matching facial surfaces of a virtual model of a side impression with facial surfaces of the virtual model of the upper jaw and with facial surfaces of the virtual model of the lower jaw. FIGS. 6A and 6B schematically illustrate block diagrams of example computing systems 600, 601, respectively. The systems 600, 601 each comprise a modeling computer 602, a seamier 604, and an optional fabrication unit 606. In some embodiments, the modeling computer 602 aligns the virtual models in the bite position and stores the aligned virtual model in a storage device such as the mass storage device 6021 or the memory 6026, each described more fully below. In some embodiments, the modeling computer 602 is used to design orthodontic appliances, to plan or adjust movement of teeth with orthodontic appliances, to model dental prostheses (e.g., abutments, copings, crowns, inlays, overlays, veneers, bridges, frameworks, etc.), and other dental or orthodontic modeling. The scanner 604 is used to scan or image impressions of the patient's dentition. The impressions may be scanned by the entity that took the impression or may be transferred to a laboratory for scanning. The scanner 604 may comprise a laser scanner, a white light scanner, a destructive scanner, etc. The scanner 604 may be configured to scan negative impressions and/or positive impressions. In some embodiments, the fabrication unit 606 can be used to fabricate orthodontic appliances or dental prostheses based on output from the modeling computer 602. For example, the fabrication unit 606 may comprise tools for milling, stereolithography, laser machining, molding, etc.

In certain embodiments, the fabrication unit 606 is configured to produce an abutment, for example as described in U.S. Pat. Nos. 5,180,303, 5,527,182, and 5,674,069, each incorporated herein by reference in its entirety. In certain embodiments, the fabrication unit 606 is configured to produce a coping and/or a crown, for example as described in U.S. Pat. Nos. 5,092,022 and 6,398,554 and U.S. Patent Pub. No. 2005/0177266, each incorporated herein by reference in its entirety. In certain embodiments, the fabrication unit 606 is configured to produce a framework and/or a bridge, for example as described in U.S. Pat. Nos. 6,694,212 and 7,228,191, each incorporated herein by reference in its entirety. In certain embodiments, the fabrication unit 606 is configured to produce a tooth model, for example as described in U.S. Pat. No. 7,118,375 and U.S. Patent Pub. No. 2007/0154867, each incorporated herein by reference in its entirety. In certain such embodiments, the tooth model may comprise reference markers indicating that the upper jaw and the lower jaw are in the bite position.

The systems 600, 601 can be a fixed system or mobile device. The computing systems 600, 601 may be used to implement one or more of the systems and methods described herein. In addition, in some embodiments, the computing systems 600, 601 are configured to process image files. Those of skill in the art will appreciate that the functionality provided for in the units, components, and modules of computing systems 600, 601 may be combined into fewer units, components, and modules or further separated into additional units, components, and modules.

In certain embodiments, the systems and methods described herein are embodied in part or in whole in software that is running on a computing device. The functionality provided for in the units, components, and modules of the computing device may comprise one or more units, components, and/or modules. For example, the computing device may comprise multiple central processing units (CPUs) and a mass storage device, such as may be implemented in an array of servers.

In general, the term "module," as used herein, refers to logic embodied in hardware or firmware, or to a collection of software instructions, possibly having entry and exit points, written in a programming language, such as, for example, Java, C, C++, combinations thereof, and the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

The modeling computer 602 comprises a central processing unit ("CPU") 6024, which may comprise a conventional microprocessor. The modeling computer 602 further comprises a memory 6025, such as random access memory ("RAM") for temporary storage of information and/or a read only memory ("ROM") for permanent storage of information, and a mass storage device 6021, such as a hard drive, diskette, or optical media storage device. The modules of the modeling computer 602 may be connected using a standards-based bus system such as, for example, Peripheral Component Interconnect (PCI), Microchannel, SCSI, Industrial Standard Architecture (ISA), and/or Extended ISA (EISA) architectures.

The modeling computer 602 comprises one or more input/output (I/O) devices and interfaces 6023, such as a keyboard, mouse, trackball, touch pad, pen, stylus, graphics tablet, touch screen, voice recognition system, switch, button, and/or printer. In some embodiments, the I/O devices and interfaces 6023 comprise one or more display devices, such as a monitor, that allows the visual presentation of data to a user. More particularly, a display device may provide for the presentation of GUIs, application software data, and multimedia presentations. The display device may comprise a cathode-ray tube (CRT), a liquid crystal display (LCD), a plasma display, a digital light processor (DLP), or other types and/or combinations of displays. In the embodiment illustrated in FIG. 6A, the I/O devices and interfaces 6023 also provide a communications interface to various external devices through a network 608. The modeling computer 602 may also comprise one or more multimedia devices 6021, such as, for example, speakers, video cards, graphics accelerators, and microphones. In some embodiments, the modeling computer 602 comprises a mainframe computer suitable for controlling and/or communicating with large databases, performing high volume transaction processing, and generating reports from large databases.

The modeling computer 602 may run on a variety of computing devices, such as, for example, a server, a Windows server, a Structure Query Language (SQL) server, a Unix server, a personal computer, a mainframe computer, a laptop computer, a cell phone, a personal digital assistant, a kiosk, an audio player, and so forth. The modeling computer 602 is generally controlled and coordinated by operating system software, such as z/OS, Windows 95, Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In some embodiments, the modeling computer 602 is controlled by a proprietary operating system. Conventional operating systems control and schedule computer processes for execution, perform memory management, provide file system, networking, and I/O services, and provide a user interface, such as a graphical user interface (GUI), among other things.

The modeling computer 602 of certain embodiments comprises an alignment module 6027 configured to perform one or more of the alignment functions or method steps described herein. For example, in some embodiments the alignment module 6027 is configured to align the virtual model of an upper jaw and a virtual model of a lower jaw in a bite position by matching facial surfaces of a virtual model of a side impression with the same facial surfaces of the virtual model of the upper jaw and with the same facial surfaces of the virtual model of the lower jaw. As described below with respect to FIG. 6A, for example, the alignment module 6027 or portions thereof may reside on a computer of the scanner 604 or a computer connected to the scanner 604 instead of or in addition to residing on the modeling computer 602. In some embodiments, for example, substantially all of the functionality of the alignment module 6027 resides on a computer of the scanner or a computer connected to the scanner 604. In other embodiments, some of the functionality of the alignment module 6027 resides on the modeling computer 602 and some of the functionality of the alignment module 6027 resides on a computer of the scanner 604 or a computer connected to the scanner 604. In some embodiments, one on more aspects and/or functionalities of the alignment module 6027 can be divided up into subcomponents that can reside within the same or different components.

In the embodiment of FIG. 6A, the modeling computer 602 is coupled to a network 608, such as a local area network, a wide area network, the Internet, etc. via, for example, a wired communication link, a wireless communication link, or combination thereof. The network 608 communicates with various computing devices and/or other electronic devices coupled to the network 608 via wired or wireless communication links.

Access to the modeling computer 602 may be provided through a web-enabled user access point such as personal computer, cellular phone, laptop computer, server, computer workstation, local area network of individual computers, interactive kiosk, personal digital assistant, interactive wireless communication device, embedded computing device, or other device capable of connecting to the network 608. Such a device may have a browser module implemented as a module that uses text, graphics, audio, video, and other media to present data and to allow interaction with data via the network 608.

The network 608 is in communication with the scanner 604 and the fabrication unit 606. The scanner 604 comprises and/or is connected to a computer comprising some or all of the components described above with respect to the modeling computer 602 (e.g., mass storage device, multimedia devices, I/O devices and interfaces, central processing unit, system memory) and can communicate with the modeling computer 602 via the network 608. In certain such embodiments, the computer connected to the scanner 604 aligns the virtual models of the impressions in the bite position and stores the aligned virtual model in a storage device. The bite position model may then be transferred to the modeling computer 602 over the network 608. In some embodiments, the computer connected to the scanner 604 transfers scan data to the modeling computer 602 over the network 608, and then the modeling computer 602 aligns the virtual models of the impressions in the bite position and stores the aligned virtual model in a storage device. The fabrication unit 606 also comprises a computer comprising some or all of the components described above with respect to the modeling computer 602 (e.g., mass storage device, multimedia devices, I/O devices and interfaces, central processing unit, system memory) and can communicate with the modeling computer 602 via the network 608. In some embodiments, data may be transferred between the modeling computer 602, the computer of the scanner 604, and the computer of the fabrication unit 606 using a portable storage medium or device (e.g., optical disk, magnetic disk, flash drive). In some embodiments, the scanner 604 is proximate to the modeling computer 602 (e.g., being in the same office, building, or campus). In some embodiments comprising a fabrication unit 606, the modeling computer 602 is proximate to the fabrication unit 606 (e.g., being in the same office, building, or campus). In some embodiments comprising a fabrication unit 606, the scanner 604 and the modeling computer 602 are both proximate to the fabrication unit 606 (e.g., being in the same office, building, or campus).

In some embodiments, the modeling computer 602 comprises a physical or logical connection established between a remote microprocessor and a mainframe host computer for the express purpose of uploading, downloading, or viewing interactive data and databases on-line in real time. The remote microprocessor may be operated by an entity operating the modeling computer 602, including the client server systems or the main server system. In some embodiments, terminal emulation software may be used on the microprocessor for participating in the microprocessor-mainframe link. In some embodiments, a computer program product comprising computer program code means for executing the method steps described herein when the computer program code means are run by an electronic device having computer capabilities. The electronic device may e.g. be a computer, such as a lap top or desk top computer.

In the embodiment illustrated in FIG. 6B, the scanner 604 and the optional fabrication unit 606 are directly connected to the modeling computer 602. In certain such embodiments, the scanner converts the impressions into virtual models of the impressions and provides the virtual models of the impressions to the modeling computer 602, the modeling computer 602 aligns the virtual models of the impressions in the bite position and is used to design a dental prosthesis using the bite position model, and the modeling computer 602 provides the fabrication unit 606 with instructions for fabricating the dental prosthesis.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. Foe example, certain techniques described herein may be implemented in hardware, software, or a combination thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. A computer-implemented method of aligning a first virtual model of at least a portion of an upper jaw of a patient's mouth and a second virtual model of at least a portion of a lower jaw of the patient's mouth in a bite position and for designing a prosthesis using the aligned virtual models, the method comprising:

forming a third virtual model of a facial side region based on data from scanning, in a single scan, an impression resulting from material applied to the facial surfaces of the upper jaw and the lower jaw with the upper jaw and the lower jaw in the bite position and including an area with a prepared residual tooth or an edentulous area, the third virtual model comprising scanned impression data of a side impression portion of the impression material comprising facial side surfaces of the upper jaw and the lower jaw only on the same side of the mouth, the side impression portion comprising a site prepared to receive said prosthesis and adjacent teeth, wherein said site comprises at least one of the prepared residual tooth and the edentulous area and said side impression portion includes a projection where the impression material flowed around the prepared residual tooth or into the edentulous area, such that the third virtual model comprises a model of the site prepared to receive said prosthesis and of adjacent teeth and information about the projection; and wherein the third virtual model of the facial side region is substantially free of occlusive surfaces of the adjacent teeth, while the projection includes information about the occlusal surfaces of a tooth opposite the prepared residual tooth or the edentulous area;

geometric surface matching facial surfaces of the first virtual model and the second virtual model with facial surfaces of the third virtual model, wherein the geometric surface matching is performed proximate and including the area with the prepared residual tooth or the edentulous area, the geometric surface matching comprising selecting points on the facial surfaces of the third virtual model, computing a transformation that matches the selected points to points on the facial surfaces of the first virtual model and the second virtual model, and minimizing the sum of squared distances between matched points; and based on said geometric surface matching, outputting an aligned virtual model of the first virtual model and the second virtual model aligned in the bite position, such that only three sets of virtual modeling data are utilized for outputting the aligned virtual model, the three sets consisting of the first virtual model of the upper jaw, the second virtual model of the lower jaw, and the third virtual model of the facial side region, the method performed programmatically by a computing system that comprises one or more physical computers and the method further comprising designing the prosthesis using the aligned virtual models.

2. The method of claim 1, wherein the prosthesis comprises an abutment, a coping, a crown, an inlay, an overlay, a bridge, or a framework.

3. The method of claim 1, wherein the first virtual model of the upper jaw comprises a model of a part of the upper jaw proximate to the site and wherein the second virtual model of the lower jaw comprises a model of a part of the lower jaw proximate to the site, wherein the matching comprises using at least one of: the facial surfaces of the first virtual model of the upper jaw at the part of the upper jaw and the facial surfaces of the second virtual model of the lower jaw at the part of the lower jaw.

4. The method of claim 1, wherein the facial surfaces of the third virtual model of the facial side region comprise at least one of: tooth surfaces and soft tissue surfaces.

5. The method of claim 1, wherein the prosthesis comprises a veneer.

6. The method of claim 1, the selected points on the facial surfaces of the third virtual model being evenly distributed across the facial surfaces of the third virtual model.

7. The method of claim 1, the selected points on the facial surfaces of the third virtual model being clustered on a portion of the facial surfaces.

8. The method of claim 1, the selected points on the facial surfaces of the third virtual model spanning facial surfaces of hard tissue and soft tissue.

9. The method of claim 1, the geometric surface matching further comprising filtering based on distance distribution.

10. The method of claim 1, wherein selecting points on the facial surfaces of the first virtual model and the second virtual model includes user input.

11. The method of claim 1, wherein the method is fully automated without user input.

12. Non-transitory computer storage having stored thereon executable program code that directs a computing system comprising one or more computers to perform the method of claim 1.

13. A computing system comprising at least one physical computer configured to perform:
receiving a first virtual model of at least a portion of an upper jaw of a patient's mouth, and a second virtual model of at least a portion of a lower jaw of the patient's mouth;
forming a third virtual model of a facial side region based on data from scanning an impression resulting from material applied to the facial surfaces of the upper jaw and the lower jaw with the upper jaw and the lower jaw in the bite position and including an area with a prepared residual tooth or an edentulous area, the third virtual model comprising scanned impression data of a side impression portion of the impression material comprising facial side surfaces of the upper jaw and the lower jaw only on the same side of the mouth, the side impression portion comprising a site prepared to receive a restoration and adjacent teeth, wherein said site comprises at least one of the prepared residual tooth and the edentulous area and said side impression portion includes a projection where the impression material flowed around the prepared residual tooth or into the edentulous area, such that the third virtual model comprises information about the projection and adjacent teeth; and wherein the virtual model of the facial side region is substantially free of occlusive surfaces of the adjacent teeth, while the projection includes information about the occlusal surfaces of a tooth opposite the residual tooth or the edentulous area;
geometric surface matching facial surfaces of the first virtual model and the second virtual model with facial surfaces of the third virtual model, the geometric surface matching comprising
selecting points on the facial surfaces of the first virtual model and the second virtual model,
computing a transformation that matches the selected points to points on the facial surfaces of the third virtual model, and
minimizing the sum of squared distances between matched points; and based on said geometric surface matching, outputting an aligned virtual model of the first virtual model and the second virtual model aligned in the bite position, such that only three sets of virtual modeling data are utilized to output the aligned virtual model, the three sets consisting of the first virtual model of the upper jaw, the second virtual model of the lower jaw, and the third virtual model of the facial side region.

14. The system of claim 13, the selected points on the facial surfaces of the third virtual model being evenly distributed across the facial surfaces of the first virtual model and the second virtual model.

15. The system of claim 13, the selected points on the facial surfaces of the third virtual model being clustered on a portion of the first virtual model and the second virtual model.

16. The system of claim 13, the selected points on the facial surfaces of the third virtual model spanning facial surfaces of hard tissue and soft tissue.

17. The system of claim 13, the geometric surface matching further comprising filtering based on distance distribution.

* * * * *